United States Patent [19]

Yen

[11] 4,002,618
[45] Jan. 11, 1977

[54] 2,2-DIPHENYL-5-(4-SUBSTITUTED-PIPERIDINO)-3-TRANS-PENTENENITRILES
[75] Inventor: Chung H. Yen, Skokie, Ill.
[73] Assignee: G. D. Searle & Co., Chicago, Ill.
[22] Filed: Feb. 23, 1976
[21] Appl. No.: 660,205
[52] U.S. Cl. .................. 260/240 R; 260/293.75; 424/267
[51] Int. Cl.² .................................. C07D 211/06
[58] Field of Search .............. 260/240 R, 293.75

[56] References Cited
UNITED STATES PATENTS

| | | |
|---|---|---|
| 3,539,579 | 11/1970 | Janssen .................... 260/293.75 |
| 3,594,401 | 7/1971 | Cavalla et al. ............. 260/293.75 |
| 3,790,581 | 2/1974 | Kreider .................... 260/293.71 |
| 3,847,923 | 11/1974 | Kreider .................... 260/281 |
| 3,847,926 | 11/1974 | Beltran .................... 260/293.75 |

*Primary Examiner*—Arthur P. Demers
*Attorney, Agent, or Firm*—John J. Kolano; Albert Tockman

[57] ABSTRACT

This invention encompasses novel 2,2-diphenyl-5-(4-substituted-piperidino)-3-trans-pentenenitriles. These compounds are useful anti-diarrheal agents and also possess analgesic activity.

5 Claims, No Drawings

2,2-DIPHENYL-5-(4-SUBSTITUTED-PIPERIDINO)-3-TRANS-PENTENENITRILES

The present invention is concerned with 2,2-diphenyl-5-(4-substituted-piperidino)-3-trans-pentenenitriles. More particularly, this invention is concerned with compounds of the formula

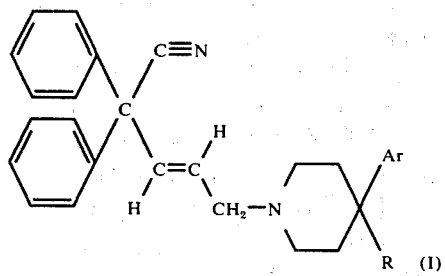

wherein Ar is selected from the group consisting of phenyl, monosubstituted lower alkylphenyl wherein the alkyl portion contains 1 to 6 carbon atoms, and monosubstituted halophenyl; and R is selected from the group consisting of hydrogen, hydroxy, cyano, lower alkoxy carbonyl containing 2 to 7 carbon atoms, and carboxy.

Particularly preferred compounds of this invention are those of the formula

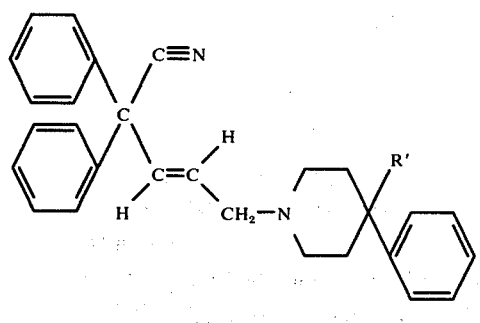

wherein R' is selected from the group consisting of hydroxy, lower alkoxy carbonyl and carboxy.

The lower alkyl groups referred to above contain 1 to 6 carbon atoms and are exemplified by methyl, ethyl, propyl, butyl, pentyl, hexyl and the corresponding branched-chain isomers thereof. The lower alkoxycarbonyl groups likewise contain 2 to 7 carbon atoms and are typified by methoxycarbonyl, ethoxycarbonyl, propoxycarbonyl, and the like.

The halo atoms encompassed by formula (I) include fluoro, chloro and bromo.

Equivalent to the compounds of formulas (I) and (II) for the purposes of the invention are the pharmaceutically acceptable acid addition salts thereof. Such acid addition salts can be derived from a variety of inorganic and organic acids such as sulfuric, phosphoric, hydrochloric, hydrobromic, hydroiodic, sulfamic, citric, lactic, pyruvic, oxalic, maleic, succinic, tartaric, cinnamic, acetic, benzoic, salicylic, gluconic, ascorbic and related acids.

Also equivalent to the enformulated compounds for the purposes of this invention are solvates thereof in which biologically insignificant amounts of solvent are present.

The compounds of the present invention are useful in consequence of their valuable pharmacological properties. They are, for example, potent anti-diarrheal agents as evidenced by their ability to inhibit gastrointestinal motility as set out in the following tests.

Charcoal Meal Test

The method used for this assay is a modification of the techniques previously described by Macht and BarbaGose, J. Amer. Pharm. Ass., 20, 558 (1931), and Janssen and Jageneau, J. Pharm. Pharmacol., 9, 381 (1957). Details are as follows:

A group of six, male Charles River mice weighing 20–25 g. which have been previously fasted for 24 hours are pretreated with the test compounds administered orally as a solution in water or suspended in 0.5% methyl cellulose. A constant volume of 10 ml./kg. is employed. 30 minutes following administration of the test compounds, the animals are given a single oral dose of charcoal which consists of 0.2 ml. per mouse of 10% charcoal suspended in 1.0% methyl cellulose. Three and a half hours after charcoal administration, the animals are sacrificed and the cecum examined for the absence or presence of charcoal on an all-or-none basis.

The median effective dose ($ED_{50}$) is then calculated for each compound using the logistic method of Berkson (1953).

Castor Oil-Induced Diarrhea in the Rat

Adult Charles River male rats are fasted in community cages for 24 hours prior to the test, with free access to water. The test compound is then administered intragastrically (suspended on 0.5% methyl cellulose) one hour prior to the intragastric administration of a dose of 1.0 ml. castor oil per rat. The rats are then observed for the presence or absence of diarrhea at hourly intervals for up to 8 hours past the castor oil administration. Using the method of Berkson (1953), the median effective dose ($ED_{50}$) values are calculated at each hourly interval for the test compound.

In addition to their anti-diarrheal activity, certain of the compounds of this invention demonstrate analgesic activity at the test doses. The assessment of this activity is conducted by the following assay:

Tail Clip Test

A special clip is applied to the base of the tail of an adult male mouse weighing 18–25 grams and the time for the animal to turn around to bite at the clip is measured. The sensitivity of each mouse is determined one-half hour prior to drug administration and only those mice attempting to bite the clip are included in the experiment. The test compound is then administered either intragastrically or intraperitoneally and the response to placement of the clip is determined at 30, 60, 90 and 120 minutes after treatment. A response is considered positive if the animal takes more than 2 times the pre-drug time to bite at the clip at any of these time intervals. A test compound is considered active when 50 percent or more of the animals used show a positive response.

A representative compound of this invention which exhibits anti-diarrheal activity in the Charcoal Meal Test and analgesic activity in the Tail Clip Test is 2,2-diphenyl-5-(4-ethoxycarbonyl-4-phenylpiperidino)-3-trans-pentenenitrile.

The compounds of formula (I) may be combined with various pharmaceutical carriers to provide compositions suitable for use in the treatment of diarrhea. The dosage of these compounds is dependent upon various factors, such as the particular compound employed and the particular response obtained. Typical dosages for use as an anti-diarrheal agent vary from 0.1 to 25 mg./kg. per day administered orally.

The compounds of the present invention are conveniently prepared by reacting an alkyl halide of the formula

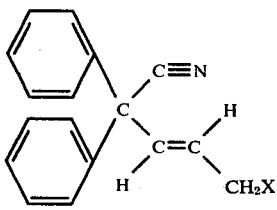

wherein X is a chloro, bromo or iodo atom with the appropriate 4-substituted piperidine of the formula

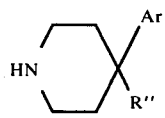

wherein R'' is selected from the group consisting of hydrogen, hydroxy, cyano, and lower alkoxycarbonyl and Ar is defined as hereinbefore. Depending on the nature of the reactants, it is possible to carry out this reaction in the presence or absence of a solvent. The use of a solvent is, however, generally preferred. An especially desirable solvent is methyl isobutyl ketone, while other possible solvents include methanol, ethanol and isopropanol. Time and temperature are not critical factors for the conduct of this reaction, typical temperatures varying from room temperature to reflux and typical times are in the range of 2-24 hours.

The compounds of formula (I) wherein R is carboxy are prepared by hydrolysis of the corresponding compound of formula (I) wherein R is lower alkoxycarbonyl. A preferred method for this preparation involves alkaline hydrolysis using sodium hydroxide.

The starting material of formula (III) is conveniently generated by the reaction of 2,2-diphenyl-3-trans-pentenenitrile with an appropriate allylic halogenating agent. A particularly preferred method of generating this starting material involves the reaction of the aforementioned 2,2-diphenyl-3-trans-pentenenitrile with N-bromosuccinimide. This reaction is usually conducted in an inert organic solvent, a particularly preferred solvent being carbon tetrachloride. The use of free-radical initiators such as infrared light and a peroxide, i.e., benzoyl peroxide, in such a reaction is desirable.

The following examples describe in detail compounds illustrative of the present invention and methods which have been devised for their preparation. It will be apparent to those skilled in the art that many modifications, both of materials and methods, may be practiced without departing from the purpose and intent of this disclosure. Throughout the examples hereinafter set forth, temperatures are given in degrees Centigrade (° C.) and relative amounts in parts by weight, except as otherwise noted.

EXAMPLE 1

A solution of 10.0 parts of 2,2-diphenyl-4-bromopentanenitrile in 47 parts pyrrolidine is heated to reflux for 17 hours under a nitrogen atmosphere. Then, the solution is cooled, and stripped in vacuo to leave a brown oil which is partitioned between ethyl ether and dilute hydrochloric acid. The ether phase is separated, washed with dilute sodium bicarbonate, dried over anhydrous sodium sulfate, and stripped in vacuo. The residual liquid is then distilled to afford, as a colorless liquid, 2,2-diphenyl-3-trans-pentenenitrile, boiling at about 115°-123° C. at 0.1 mm pressure. This compound is represented by the following structural formula.

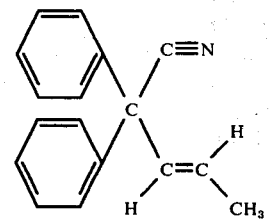

EXAMPLE 2

A solution of 5.25 parts 2,2-diphenyl-3-trans-pentenenitrile, 4.2 parts N-bromosuccinimide, and a catalytic amount of benzoyl peroxide in 80 parts carbon tetrachloride is heated under the irradiation of an infrared lamp for 4.5 hours. After cooling to 20° C., the mixture is filtered and the solid washed with 16 parts carbon tetrachloride. The filtrate and carbon tetrachloride washing are combined and treated with 50.3 parts of a 20.9% solution of 4-ethoxycarbonyl-4-phenylpiperidine in methyl isobutyl ketone and left to stand for about 18 hours. The mixture is filtered to remove the solid precipitate. The filtrate is then washed with dilute acetic acid and with dilute sodium hydroxide, dried over anhydrous sodium sulfate and stripped in vacuo. The residual oil is dissolved in ether, and the ethereal layer extracted with dilute hydrochloric acid resulting in an oil suspended in the acid layer. This acid layer is then treated with excess aqueous sodium hydroxide and extracted with ether. The ether extract is dried over anhydrous sodium sulfate and stripped in vacuo to afford a white solid. This solid is recrystallized from ether to give 2,2-diphenyl-5-(4-ethoxycarbonyl-4-phenylpiperidino)-3-trans-pentenenitrile, melting at about 100°-102.5° C. and represented by the following structural formula.

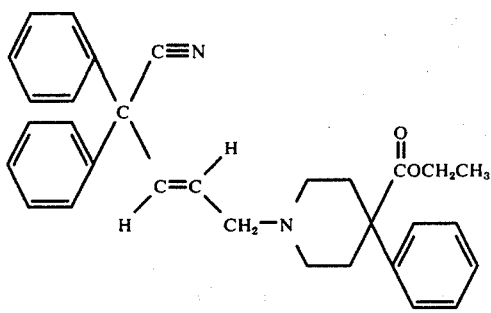

EXAMPLE 3

A mixture of 1.0 part 2,2-diphenyl-5-(4-ethoxycarbonyl-4-phenylpiperidino)-3-trans-pentenenitrile, 2.5 parts sodium hydroxide and 4.2 parts methanol is heated for 16 hours at reflux. Then, the solution is cooled and stripped in vacuo. The residue is suspended in ice-cold water, treated with excess aqueous hydrochloric acid, and extracted three times with portions of methylene chloride, resulting in a fine solid at the interface. This solid is collected by filtration, washed with water, air-dried and recrystallized from a methanolether mixture to afford 2,2-diphenyl-5-(4-carboxy-4-phenylpiperidino)-3-trans-pentenenitrile hydrochloride. This compound melts at about 266°–268° C. with gas evolution and is represented by the following structural formula.

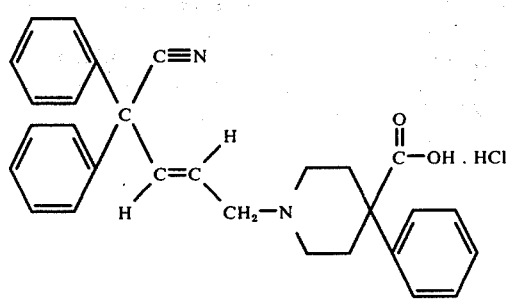

EXAMPLE 4

Repetition of the procedure of Example 2 using an equivalent quantity of 4-phenyl-4-piperidinol in place of the 4-ethoxycarbonyl-4-phenylpiperidine affords 2,2-diphenyl-5-(4-hydroxy-4-phenylpiperidino)-3-trans-pentenenitrile, melting at about 134°–136° C. This compound is represented by the following structural formula.

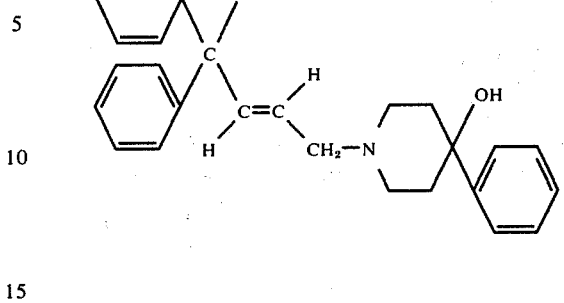

EXAMPLE 5

Substitution of an equivalent quantity of 4-(p-chlorophenyl)-4-ethoxycarbonylpiperidine for the 4-(ethoxycarbonyl)-4-phenylpiperidine of Example 2 and substantial repetition of the procedure detailed therein affords 2,2-diphenyl-5-(4-p-chlorophenyl-4-ethoxycarbonylpiperidino)-3-trans-pentenenitrile. This compound is represented by the following structural formula.

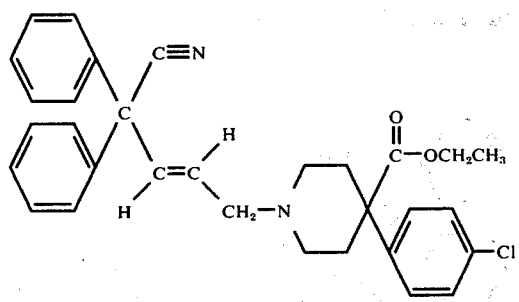

EXAMPLE 6

Using an equivalent quantity of 4-(p-tolyl)-4-piperidinol in the procedure detailed in Example 2 affords 2,2-diphenyl-5-[4-hydroxy-4-(p-tolyl)-piperidino]-3-trans-pentenenitrile. This compound is represented by the following structural formula.

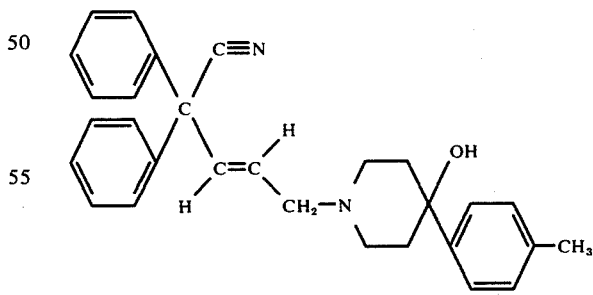

EXAMPLE 7

When an equivalent quantity of 4-cyano-4-phenylpiperidine is used in the procedure of Example 2 there is obtained 2,2-diphenyl-5-(4-cyano-4-phenylpiperidino)-3-transpentenenitrile. This compound is represented by the following structural formula.

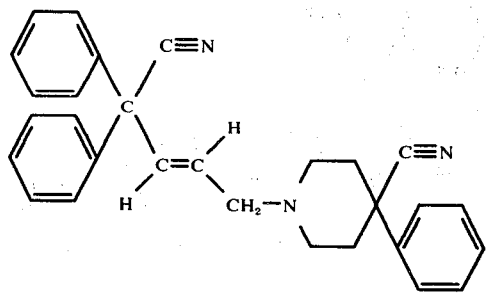

EXAMPLE 8

Substantial repetition of the procedure detailed in Example 2 using an equivalent amount of 4-phenylpiperidine affords 2,2-diphenyl-5-(4-phenylpiperidino)-3-trans-pentenenitrile represented by the following structural formula.

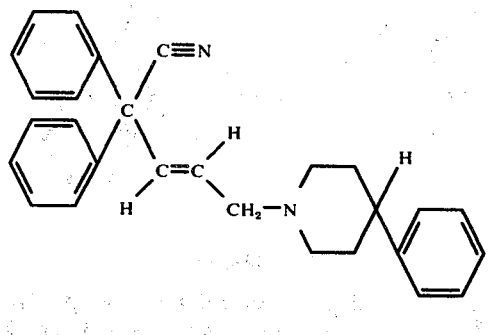

What is claimed is:

1. A compound of the formula

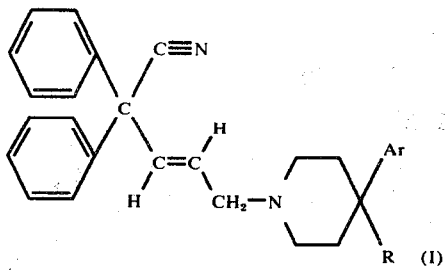

wherein Ar is selected from the group consisting of phenyl, monosubstituted lower alkylphenyl wherein the alkyl portion contains 1 to 6 carbon atoms, and monosubstituted halophenyl; and R is selected from the group consisting of hydrogen, hydroxy, cyano, lower alkoxycarbonyl containing 2 to 7 carbon atoms, and carboxy.

2. A compound according to claim 1 of the formula

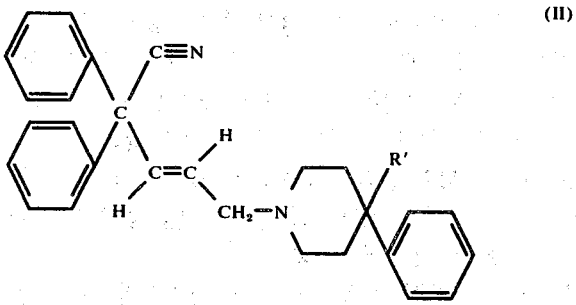

wherein R' is selected from the group consisting of hydroxy, lower alkoxy carbonyl and carboxy.

3. A compound according to claim 1 which is 2,2-diphenyl-5-(4-ethoxycarbonyl-4-phenylpiperidino)-3-trans-pentenenitrile.

4. The compound according to claim 1 which is 2,2-diphenyl-5-(4-carboxy-4-phenylpiperidino)-3-trans-pentenenitrile.

5. The compound according to claim 1 which is 2,2-diphenyl-5-(4-hydroxy-4-phenylpiperidino)-3-trans-pentenenitrile.

* * * * *